United States Patent [19]

Murdoch

[11] Patent Number: 5,400,767
[45] Date of Patent: Mar. 28, 1995

[54] LAPAROSCOPIC TELESCOPE LENS CLEANER AND PROTECTOR

[76] Inventor: Mervyn J. Murdoch, 201 Macquarie St., Hobart, Tasmania 7000, Australia

[21] Appl. No.: 30,110
[22] PCT Filed: May 13, 1992
[86] PCT No.: PCT/AUG92/00212
 § 371 Date: Mar. 15, 1993
 § 102(e) Date: Mar. 15, 1993
[87] PCT Pub. No.: WO92/20274
 PCT Pub. Date: Nov. 26, 1992

[30] Foreign Application Priority Data

May 14, 1991 [AU] Australia ............... PK6140

[51] Int. Cl.⁶ .................................... A61B 1/00
[52] U.S. Cl. .................................. 128/4; 128/7; 128/6
[58] Field of Search ...................... 128/4, 6, 7

[56] References Cited

U.S. PATENT DOCUMENTS

| 4,281,646 | 8/1981 | Kinoshita . | |
| 4,738,659 | 4/1988 | Sleiman . | |
| 4,760,838 | 8/1988 | Fukuda . | |
| 4,765,314 | 8/1988 | Kolditz . | |
| 4,959,058 | 9/1990 | Michelson | 126/4 X |
| 4,973,321 | 11/1990 | Michelson | 128/4 X |
| 4,991,565 | 2/1991 | Takahashi et al. . | |

FOREIGN PATENT DOCUMENTS 2533004 2/1976 Germany ............... 128/6

Primary Examiner—Richard J. Apley
Assistant Examiner—Beverly A. Meindl
Attorney, Agent, or Firm—Richard J. Godlewski

[57] ABSTRACT

A simple, rapid and effective device for cleaning the objective lens of a laparoscope, endoscope, coeloscope or similar telescope, without the removal of said telescope from the body cavity, is disclosed. In one embodiment, the device consists of a tube, the inner diameter of which is such that it accepts the shaft of such telescope. On the inner circumference, near to or at one end of the tube, is a ridge that can direct a flow of fluid within the tube onto the objective lens at the end of a telescope shaft inserted within the tube. At the other end of the tube there is a means of making a seal, such as a flexible O-ring, that prevents or reduces the leakage of air and/or fluid between the tube and the inserted shaft of the telescope. There is an aperture in the tube which gives access to the inside of the tube. Prior to use, the shaft of the telescope is inserted into the invention so that the end of the telescope, containing the objective lens, touches or almost touches the ridge. During operation, whenever the objective lens at the end of the telescope shaft becomes soiled or obscured, fluid is injected through the aperture via a fixture. The fluid flows between the telescope shaft and the inner wall of the tube until it reaches the ridge which directs the fluid over the objective lens, washing the lens and improving or restoring visibility.

15 Claims, 1 Drawing Sheet

LAPAROSCOPIC TELESCOPE LENS CLEANER AND PROTECTOR

TECHNICAL FIELD

This invention relates to an apparatus and method for cleaning and protecting the objective lens of a laparoscope, endoscope, or coeloscope. It is to be noted that the term "telescope" is used herein to describe a laparoscope, endoscope, coeloscope or rigid or relatively rigid optical device used for the observation of structures within a body cavity and/or procedures within a body cavity. In particular, the invention relates to an apparatus and method for cleaning and protecting the objective lens of such telescopes whilst the telescope is in use within a body cavity.

BACKGROUND ART

Certain operative procedures, particularly laparoscopy, hysteroscopy, endoscopy and coeloscopy, require the insertion into a body cavity, such as the abdominal cavity, of the objective lens of a laparoscope, endoscope, coeloscope or similar telescope in order to view features and structures within the body cavity and/or to view diagnostic or operative procedures carried out within the cavity.

Such telescopes usually consist in part of a rigid or relatively rigid rod or shaft of approximately 300–500 mm length, with an outer diameter of 5 mm to 11 mm, having an objective lens at one end and an eyepiece at the other end. The rod or shaft of the telescope contains light-transmitting glass fibres and/or rod lenses.

A prerequisite for the utilisation of such telescopes is the illumination of the structures within the body cavity with clear, bright light. To achieve this, the telescope also normally has a connection, adjacent to the eyepiece, for the attachment of an external light source which provides illumination, via light-transmitting fibres within the telescope, of the features within the body cavity.

Prior to the introduction of the telescope, the body cavity is generally inflated with a gas, usually carbon dioxide, using a gas insufflator. Subsequently a plastic or metal sleeve or sheath, often referred to as a trocar, is inserted through the wall of the cavity. These sleeves contain a means of making a seal to prevent the leakage of gas from within the body cavity. The end of the telescope containing the objective lens is inserted into the body cavity through the sleeve, the attached light-source activated and the features within the body cavity viewed through the eyepiece of the telescope or on a video monitor receiving signals from a video camera attached to the eyepiece.

The objective lens of the telescope often becomes soiled during operative procedure. Tissue particles, blood and other body fluids attach to the lens and obscure vision. In these instances, the telescope has to be removed from the body cavity and the objective lens wiped clean with a suitable cloth. During some operative procedures, the telescope may have to be removed frequently to have the lens wiped clean.

The loss of vision due to soiling of the objective lens of the telescope is a serious complication if the source of soiling is blood from a transected blood vessel, particularly an arterial vessel. The covering of the objective lens of the telescope by arterial blood is often referred to as the "red video" sign. This is particularly serious if the bleeding is extensive. The lens might be repeatedly obscured by blood or the bleed be so extensive as to not allow enough time to safely remove the telescope to wipe the lens. In such cases the procedure is often converted to an emergency "open" operative procedure.

OBJECT OF THE INVENTION

It is the object of the current invention to provide a simple, rapid and effective means of cleaning the objective lens of a laparoscope, endoscope, coeloscope or similar telescope that addresses the problems discussed above. In particular the invention allows for the rapid, effective and repeated cleaning of the objective lens without the removal of the telescope from the body cavity.

DISCLOSURE OF INVENTION

According to one aspect of the invention there is provided a device consisting of
- a tube, the inner diameter of which is such that it accepts the shaft of a laparoscope, endoscope, coeloscope or similar telescope or other rigid or relatively rigid optical devices used for the observation of structures within a body cavity;
- a ridge near one end of the inner circumference of the tube that can direct a flow of fluid within the tube towards the central axis of the tube, or onto the objective lens at the end of the telescope shaft inserted within the tube;
- a means of making a seal, such as a flexible O-ring, at the other end of the tube. The inside diameter of the seal is less than or the same as the outer diameter of the shaft of the telescope. The purpose of the seal is to prevent or reduce the leakage of air and/or fluid between the tube and the telescope shaft.
- an aperture in the tube which gives access to the inside of the tube between the seal and the ridge. The aperture is such that it allows the attachment of a fluid supply from a reservoir, such as a syringe or bulb, and/or a flexible tube from a reservoir.

Prior to the use of the telescope, the shaft of the telescope is inserted into the invention so that the end of the telescope, with the objective lens, touches or almost touches the ridge. The invention is held in place on the telescope shaft by friction due to the seal or by a thread or a clip on the invention.

The combined invention and telescope are then utilised in the same manner as the telescope would be utilised alone. That is, the combined invention and telescope shaft is inserted through a sleeve, sheath or trocar into the body cavity, the external light source attached to the telescope is activated and the features within the body cavity are viewed through the eyepiece or on a video monitor receiving signals from a video camera attached to the eyepiece.

During operation, whenever the objective lens of the telescope becomes soiled or obscured, fluid is injected from the reservoir attached to the reservoir, through the aperture and into the inside of the tube. The injected fluid flows between the telescope shaft and the inner wall of the tube until it reaches the ridge on the inner circumference of the tube. The ridge directs the fluid over the objective lens at the end of the telescope shaft. The fluid washes the lens and improves or restores visibility.

BRIEF DESCRIPTION OF DRAWINGS

The particular preferred embodiments of the invention will now be described by way of example with reference to accompanying drawings wherein.

BEST MODE OF CARRYING OUT THE INVENTION

Figure 1A:
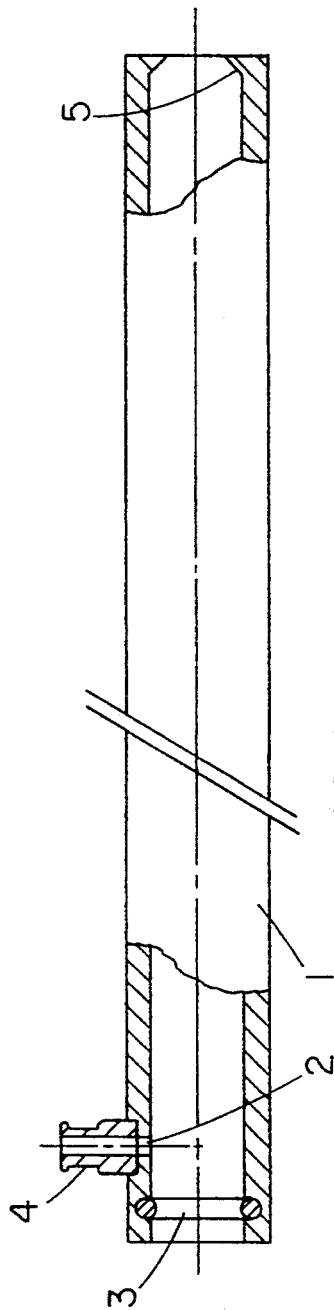
FIG. 1 shows a sketch of one embodiment of the invention, showing both an end and side view.
Figure 1B:
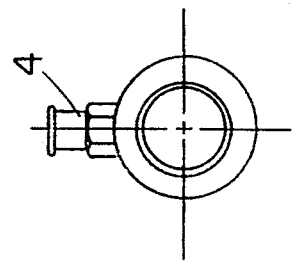

FIG. 1 shows one embodiment of the invention which consists of a tube 1 the inner diameter of which is such that it accepts the shaft of a laparoscope, endoscope, coeloscope or similar telescope. Near to or at one end of the tube 1 is a ridge 5 on the inner circumference of the tube. The ridge 5 is such that it can direct a flow of fluid within the tube towards the central axis of the tube, or onto the objective lens at the end of such a telescope shaft inserted within the tube 1. In one particular embodiment, the ridge 5 is formed by turning the edge of the tube 1 inwards to form a lip.

At the other end of the tube 1 there is a means of making a seal 3 between the inner circumference of the tube 1 and the outer circumference of the inserted shaft of the telescope. In one particular embodiment the seal 3 is a flexible O-ring situated on the inner circumference of the tube 1.

The inside diameter of the seal 3 is less than or the same as the outer diameter of the telescope shaft. The purpose of the seal 3 is to prevent or reduce the leakage of air and/or fluid between the tube 1 and the inserted shaft of the telescope.

There is an aperture 2 in the tube 1 which gives access to the inside of the tube between the seal 3 and the ridge 5. The aperture 2 is such that it allows the attachment of a fluid supply. In one embodiment, the aperture has a fixture 4 that allows the attachment of a reservoir, such as a syringe or bulb and/or a flexible tube from a reservoir.

Figure 2:
FIG. 2 shows a sketch of the side view of part of another embodiment of the invention.

FIG. 2 shows part of another particular embodiment where the means of making a seal 3 is on a separate fixture 6 attached to the end of the tube 1. There is also an aperture 2 in this fixture 6 which gives access to the inside of the tube 1 between the seal 3 and the ridge 5.

Figure 3:
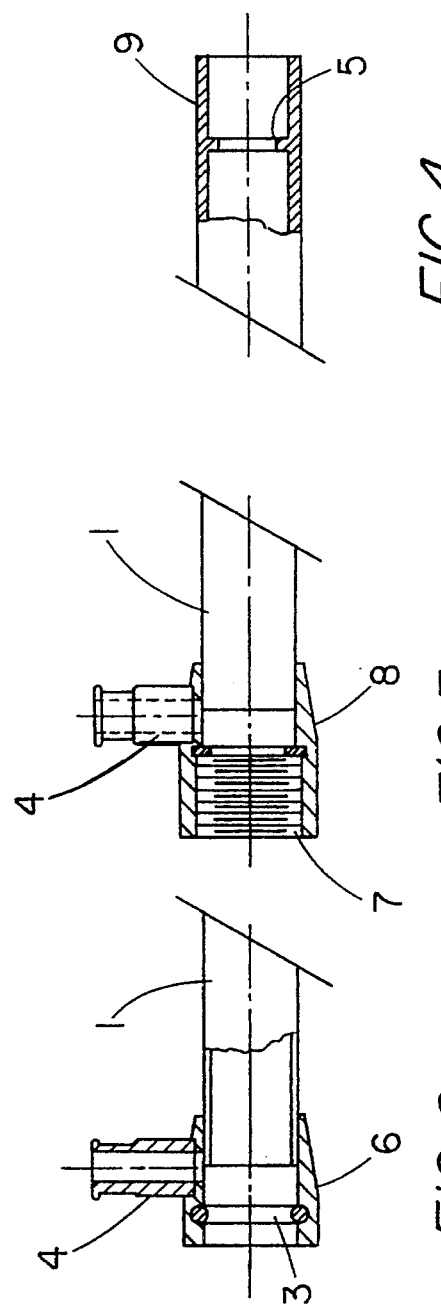
FIG. 3 shows a sketch of the side view of part of another embodiment of the invention.

FIG. 3 shows part of another particular embodiment where the means of making a seal is a compressible washer 8 adjacent to a thread 7. In one particular embodiment the attachment of a telescope or another fixture helps retain the washer 8 in place.

Figure 4:
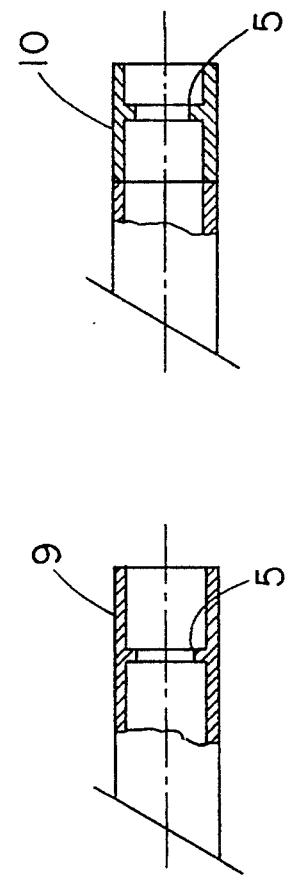
FIG. 4 shows a sketch of the side view of part of another embodiment of the invention.

FIG. 4 shows part of another particular embodiment where the length of tube 9 between the ridge 5 and adjacent end of the tube 1 is such that it additionally protects the objective lens on the end of the telescope shaft.

Figure 5:
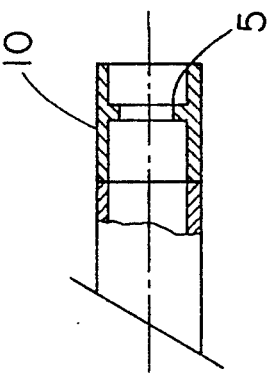
FIG. 5 shows a sketch of the side view of part of another embodiment of the invention.

FIG. 5 shows part of another embodiment where the ridge 5 is on the inner circumference of a distinct fixture 10 attached to the end of the tube 1.

The combined length of the tube 1, and the fixtures 6 and/or 10 if present, is the same as or slightly longer than or shorter than the length of the telescope shaft.

Prior to use, the shaft of the telescope is inserted into the invention so that the end of the telescope, containing the objective lens, touches or almost touches the ridge 5.

The invention is held in place on the telescope shaft by friction due to the seal 3. In another embodiment, shown in FIG. 3, the invention is held in place by a thread 7 in or on the tube 1 or in or on the fixture 6 if present.

During operation, whenever the objective lens at the end of the telescope shaft becomes soiled or obscured, fluid is injected from a reservoir through the aperture 2 and into the inside of the tube 1. The injected fluid flows between the telescope shaft and the inner wall of the tube 1 until it reaches the ridge 5 on the inner circumference of the tube. The ridge 5 directs the fluid over the objective lens at the end of the telescope. The fluid washes the lens and improves or restores visibility.

What is claimed is:

1. A lens cleaning device for a laparoscopic telescope comprising:

a tube having one end, an other end, a central axis and an inner diameter which accepts a shaft of a laparoscopic telescope;

a ridge positioned on an inner circumference of said tube proximate said one end of said tube and directing a fluid within said tube toward said central axis of said tube and over an objective lens of a laparoscopic telescope when inserted in said tube;

a seal that restricts passage of a fluid between said inner circumference of said tube and a shaft of a laparoscopic telescope, said seal being positioned between said ridge and said other end of said tube;

an aperture communicating with an inside of said tube between said seal and said ridge; and a fixture for connecting a reservoir to said aperture.

2. The device of claim 1 where said ridge on said inner circumference is contained in a fixture attached to said one end of said tube.

3. The device of claim 2 where said seal is contained in a fixture attached to said other end of said tube.

4. The device of claim 2 where said fixture attached to said one end of said tube has a thread.

5. The device of claim 3 where said fixture attached to said other end of said tube has a thread.

6. The device of claim 5 where said fixture attached to said one end of said tube has a thread.

7. The device of claim 1 where said seal is contained in a fixture attached to said other end of said tube.

8. The device of claim 7 where said fixture attached to said other end of sid tube has a thread.

9. The device of claim 1 where said other end of said tube has a thread.

10. A lens cleaning device for a laparoscopic telescope comprising:

a tube having one end, an other end, a central axis and an inner diameter which accepts a shaft of a laparoscopic telescope;

a ridge positioned on an inner circumference of said tube proximate said one end of said tube for directing a fluid toward said central axis of said tube and over an objective lens of a laparoscopic telescope when inserted in said tube, said ridge on said inner circumference being contained in a fixture attached to said one end of said tube;

a seal that restricts passage of a fluid between said inner circumference of said tube and a shaft of a laparoscopic telescope, said seal being positioned between said ridge and said other end of said tube;

an aperture communicating with an inside of said tube between said seal and said ridge; and a fixture for connecting a reservoir to said aperture.

11. The device of claim 10 where said seal is contained in a fixture attached to said other end of said tube.

12. The device of claim 10 where said fixture attached to said other end of said tube has a thread.

13. The device of claim 12 where said fixture attached to said one end of said tube has a thread.

14. A lens cleaning device for a laparoscopic telescope comprising:

a tube having one end, an other end, a central axis and an inner diameter which accepts a shaft of a laparoscopic telescope;

a ridge positioned on an inner circumference of said tube proximate said one end of said tube for directing a fluid toward said central axis of said tube and over an objective lens of a laparoscopic telescope when inserted in said tube;

a seal that restricts passage of a fluid between said inner circumference of said tube and a shaft of a laparoscopic telescope, said seal being positioned between said ridge and said other end of said tube, said seal being contained in a fixture attached to said other end of said tube;

an aperture communicating with an inside of said tube between said seal and said ridge; and a fixture for connecting a reservoir to said aperture.

15. The device of claim 14 where said fixture attached to said one end of said tube has a thread.

* * * * *